United States Patent [19]

Pápantoniou et al.

[11] 4,076,912
[45] Feb. 28, 1978

[54] TETRAPOLYMERS COMPRISING (A) UNSATURATED ACIDS (B) VINYL ESTERS (C) BRANCHED ALLYL OR METHALLYL ESTERS AND (D) VINYL ETHER OR VINYL FATTY ESTER OR LINEAR ALLYL OR METHALLYL ESTERS

[75] Inventors: Christos Pápantoniou, Epinay-sur-Seine; Jean-Claude Grognet, Gagny, both of France

[73] Assignee: L'Oreal, Paris, France

[21] Appl. No.: 674,273

[22] Filed: Apr. 6, 1976

Related U.S. Application Data

[62] Division of Ser. No. 563,460, Mar. 31, 1975, Pat. No. 3,966,403.

[30] Foreign Application Priority Data

Apr. 1, 1974 Luxembourg ........................ 69759

[51] Int. Cl.² ................... C08F 20/04; C08F 220/00; C08C 19/00; C08C 19/22
[52] U.S. Cl. .................................... 526/16; 260/885; 526/47; 526/49; 526/50; 526/317
[58] Field of Search .................. 526/317, 16, 47, 49, 526/50; 260/885

[56] References Cited

U.S. PATENT DOCUMENTS

| | | | |
|---|---|---|---|
| 3,231,534 | 1/1966 | Blades et al. ........................ | 526/332 |
| 3,455,887 | 7/1969 | Levine ................................ | 526/317 |
| 3,484,420 | 12/1969 | Chirara .............................. | 526/317 |
| 3,579,629 | 5/1971 | Pasero et al. ...................... | 526/317 |
| 3,716,633 | 2/1973 | Viout et al. ........................ | 526/317 |
| 3,810,977 | 5/1974 | Levine et al. ...................... | 424/47 |

*Primary Examiner*—Herbert J. Lilling
*Attorney, Agent, or Firm*—Cushman, Darby & Cushman

[57] ABSTRACT

Copolymer of (a) an unsaturated acid having the formula $R-CH = CH-(CH_2-O-CH_2)_n-COOH$ wherein $n = 0$ or $1$, and when $n = 0$, $R = CH_3$ and when $n = 1$, $R = H$, (b) a vinyl ester of the formula

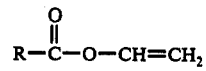

wherein R is $CH_3$ or $C_2H_5$, (c) at least one branched allyl or methallyl ester of the formula

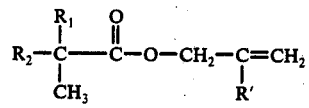

wherein R' represents hydrogen or $CH_3$, $R_1$ represents a saturated hydrocarbon chain, linear or branched, having 1-6 carbon atoms and $R_2$ represents $CH_3CH(CH_3)_2$, with the proviso that the sum of the number of the carbon atoms in $R_1+R_2$ is equal to or less than 7 and (d) a monomer selected from the group consisting of a vinyl ether of the formula $CH_2 = CH-O-R_3$ wherein $R_3$ is linear or branched alkyl having 1-12 carbon atoms, a vinyl ester having a fatty chain and having the formula

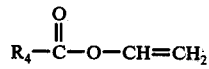

wherein $R_4$ is linear alkyl having 7-11 carbon atoms and a linear allyl or methallyl ester of the formula

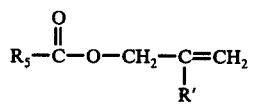

wherein R' is hydrogen or $CH_3$ and $R_5$ is linear alkyl having 1-11 carbon atoms. The copolymer is employed with a cosmetic carrier or vehicle to provide a cosmetic composition for the hair, such as a hair lacquer or hair setting lotion, generally in an amount of about 1-4 weight percent of the composition.

13 Claims, No Drawings

TETRAPOLYMERS COMPRISING (A) UNSATURATED ACIDS (B) VINYL ESTERS (C) BRANCHED ALLYL OR METHALLYL ESTERS AND (D) VINYL ETHER OR VINYL FATTY ESTER OR LINEAR ALLYL OR METHALLYL ESTERS

This is a division of application Ser. No. 563,460, filed Mar. 31, 1975, now U.S. Pat. No. 3,966,403.

The present invention relates to new copolymers and particularly to tetrapolymers, pentapolymers or higher polymers which are usefully employed in the production of cosmetic compositions such as hair lacquer or hair setting lotion compositions.

It is known that natural or synthetic resins, most often solubilized in a hydroalcoholic or alcoholic cosmetic carrier, are currently employed to provide hair lacquer or hair setting lotion compositions.

Representative resins and polymers used up to now include, in particular, polyvinylpyrrolidone, copolymers of vinylpyrrolidone and vinyl acetate, copolymers of acrylic esters and unsaturated monocarboxylic acid, copolymers of maleic anhydride and vinyl alkyl ether, copolymers resulting from the copolymerization of vinyl acetate, crotonic acid and other unsaturated monomers such as vinyl esters having from 13-25 carbon atoms and allyl or methallyl esters having from 14 to 27 carbon atoms, as well as copolymers of vinyl acetate, crotonic acid and branched vinyl esters having at least 7 carbon atoms.

With regard to these latter polymers, the copolymers of the present invention exhibit numerous advantages.

First, the copolymers of the present invention can be obtained in a more economical manner and with great purity. Moreover, it is possible in accordance with this invention to obtain polymers having a molecular weight clearly lower than those previously produced, without it being necessary to use chain regulating agents. This is quite desirable when the copolymer is to be used in cosmetics especially since it has been observed that when such chain regulating agents are employed the resulting copolymer is often contaminated to the point where its use in cosmetic compositions is virtually excluded because of residual odors or because of parasitic reactions which occur between such chain regulated polymers and other components in cosmetic compositions.

Although other methods have been known to regulate the polymer chain, i.e. mass or suspension polymerization which employs significant quantities of initiators, or solution polymerization, these methods are difficult to put into practice and are less economical than the process of the present invention.

According to the present invention, the polymerization of the different comonomers provides, without having to have recourse to chain regulating means, copolymers having a molecular weight not exceeding 40,000 and such copolymers in the cosmetic field exhibit significantly quite better qualities than those previously described and currently used in this field.

In effect, the copolymers according to the present invention have, in addition to the cosmetic qualities required for all hair lacquers or hair setting lotions, the long sought after characteristic of being easily removed by brushing and combing of the hair.

Finally the copolymers of the present invention exhibit excellent solubility in alcohols, such as ethyl or isopropyl alcohol, thereby enabling a reduction, in significant proportions, of the quantity of this type of solvent in the ultimate cosmetic formulation.

The present invention is thus related to an industrial product which comprises a copolymer resulting from the copolymerization of (a) an unsaturated acid having the formula

$$R-CH=CH-(CH_2-O-CH_2)_n-COOH \quad \text{(I)}$$

wherein
$n = 0$ or 1, and
when $n = 0$, $R = CH_3$ and
when $n = 1$, $R = H$, (b) a vinyl ester of the formula

(II)

wherein R is $-CH_3$ or $-C_2H_5$, (c) at least one branched allyl or methallyl ester of the formula

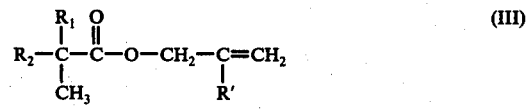

(III)

wherein R' represents hydrogen or $-CH_3$, $R_1$ represents a saturated hydrocarbon chain, linear or branched, having 1-6 carbon atoms and $R_2$ represents $-CH_3$ or $-CH(CH_3)_2$, with the proviso that the sum of the number of the carbon atoms in $R_1 + R_2$ is equal to or less than 7 and (d) a monomer selected from the group consisting of
(i) a vinyl ether of the formula $$CH_2=CH-O-R_3 \quad \text{(IV)}$$

wherein $R_3$ is linear or branched alkyl having 1-12 carbon atoms, (ii) a vinyl ester having a fatty chain of the formula

(V)

wherein $R_4$ is linear alkyl having 7-11 carbon atoms, and (iii) a linear allyl or methallyl ester of the formula

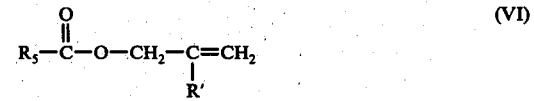

(VI)

wherein R' is hydrogen or $-CH_3$ and $R_5$ is linear alkyl having 1-11 carbon atoms.

Further, in accordance with the present invention the said copolymers result from the copolymerization of 2-15, preferably 4-12, weight percent of the unsaturated acid of formula (I), 55-89.5, preferably 65-85, weight percent of the vinyl ester of formula (II), 8-20, preferably 10-17, weight percent of at least one allyl or methallyl ester of formula (III) and 0.5-10, preferably 1-6, weight percent of the monomer selected from the vinyl ether of formula (IV), the vinyl ester of formula (V) or the allyl or methallyl ester of formula (VI).

Representative unsaturated acids of formula I include crotonic acid and allyloxyacetic acid.

Representative vinyl esters of formula II include vinyl acetate and vinyl propionate.

Representative branched allyl or methallyl esters of formula III include allyl dimethyl propanoate, methallyl dimethyl propanoate, allyl 2,2-dimethyl pentanoate, methallyl 2,2-dimethyl pentanoate, allyl 2,2-dimethyl hexanoate, methallyl 2,2-dimethyl hexanoate, allyl 2,2-dimethyl octanoate, methallyl 2,2-dimethyl octanoate, allyl 2-isopropyl-2,3-dimethyl butyrate and methallyl 2-isopropyl-2,3-dimethyl butyrate.

Representative vinyl ethers of formula (IV) include methyl vinyl ether, ethyl vinyl ether, isopropyl vinyl ether, tertio-butyl vinyl ether, octyl vinyl ether and dodecyl vinyl ether.

Representative vinyl esters having a fatty chain of formula (V) include vinyl octanoate, vinyl decanoate and vinyl dodecanoate.

Representative linear allyl or methallyl esters of formula (VI) include allyl acetate, methallyl acetate, allyl octanoate, methallyl octanoate, allyl decanoate, methallyl decanoate, allyl dodecanoate and methallyl dodecanoate.

The copolymers of the present invention have, preferably, a molecular weight ranging between about 15,000 and 40,000.

In a particular embodiment of the present invention the copolymers are crosslinked with the aid of a crosslinking agent present in an amount between 0.1–1.2 weight percent.

Representative crosslinking agents that can be used include diallylether diethylene glycol, tetra allyloxyethane, triallyl ether of trimethylol propane, the diacrylates or dimethacrylates of diols such as ethylene glycol.

Crosslinking of the copolymers is particularly recommended when it is desired to obtain copolymers having a higher viscosity.

The present invention has also for an object a new industrial product comprising the copolymers described above, the acid function of which is neutralized with the aid of an organic base such as monoethanol amine, diethanolamine, triethanolamine, isopropanolamine, morpholine, as well as certain amino alcohols, such as 2-amino-2-methyl-1propanol and 2-amino-2-methyl-1,3-propanediol.

In accordance with the present invention, the copolymers can advantageously be neutralized with one of the bases mentioned above in a quantity equal, for example, to 10–150 percent and preferably from 50–120 percent of the quantity corresponding to stoichiometric neutralization.

The copolymers according to the present invention can be prepared by liquid phase copolymerization, for example, in a solvent such as alcohol or benzene. However, it is preferable to carry out the polymerizatin reaction in mass, or in suspension, in a medium such as water.

The polymerization reaction can be effected in the presence of a polymerization catalyst such as benzoyl peroxide, lauroyl peroxide or azo bis isobutyronitrile, the concentration of the catalyst being between, for example, 0.5–6 percent, preferably between 1–4 percent by weight relative to the total weight of the monomers being reacted.

The polymerization in suspension which yields copolymers in the form of pearls is carried out as described above in water and in the presence of a protective colloid such as polyvinyl alcohol or polyacrylic acid or hydroxyethyl cellulose.

The concentration of the protective colloid can be, for example, between 0.1–1 percent by weight relative to the total weight of the monomers being polymerized.

The present invention also relates to a novel industrial product comprising a cosmetic composition characterized by the fact that it contains at least one copolymer, as defined above, optionally neutralized, in solution in an appropriate cosmetic vehicle or carrier.

The cosmetic composition in accordance with the present invention can be, for example, a hair lacquer present or not in the form of an aerosol, a hair setting lotion or a hair treating composition.

As an example, an aerosol hair lacquer composition can be produced by packaging under pressure in an aerosol container, 1–4 weight percent of a copolymer of the present invention, optionally neutralized; 6–45 and preferably 8–25 weight percent of a lower alkanol; and 54–90 weight percent of a liquified gaseous propellant, such as dichlorodifluoromethane and trichlorofluoromethane and mixtures thereof.

Preferably the lower alkanol is ethyl or isopropyl alcohol.

A hair setting lotion composition, in accordance with the present invention, can be provided by introducing into a hydroalcoholic solution containing about 20–66 percent alcohol, 1–3 weight percent of a copolymer of the present invention. Preferably, the said copolymer is neutralized as disclosed above.

The cosmetic composition in accordance with the present invention can also contain conventional cosmetic adjuvants such as perfumes, dyes, preservatives, plasticizers, cationic products, non-ionic products, silicones to improve the brilliance or other cosmetic resins.

The following non-limiting examples illustrate the present invention. Unless otherwise stated, all parts and percentages are by weight.

EXAMPLE 1

Preparation of a copolymer of 10% crotonic acid, 72% vinyl acetate, 15% allyl dimethyl propanoate and 3% vinyl dodecanoate.

Into a 500 ml round bottomed flask fitted with a mechanical agitator, a nitrogen lead-in tube, a condenser and a thermometer, there are introduced 10 g of crotonic acid, 72 g of vinyl acetate, 15 g of allyl dimethyl propanoate and 3 g of vinyl dodecanoate. To the resulting mixture there are added 1.2 g of benzoyl peroxide and 200 g of water containing 1.6 g of Cellosize. The resulting mixture is heated to reflux, with agitation, for 10 hours. The resulting tetrapolymer is recovered in the form of pearls. Yield - 90%; Acid Index - 74; Viscosity - 2.08 cp (in a 5% solution in dimethyl formamide, DMF, at 34.6° C).

EXAMPLE 2

Preparation of a copolymer of 10% crotonic acid, 75% vinyl acetate, 14% allyl dimethyl propanoate and 1% vinyl dodecanoate.

This polymer is prepared essentially in accordance with the method set forth in Example 1 including, of course, the presence of 1.2 g of benzoyl peroxide. Yield of the tetrapolymer - 90%; Acid Index - 74; Viscosity - 1.98 cp (5% DMF at 34.6° C).

EXAMPLE 3

The method of Example 1 is repeated except that the monomers employed were 75 g of vinyl acetate, 10 g of crotonic acid, 12 g of allyl dimethyl propanoate and 3 g of vinyl dodecanoate, in the presence of 1.2 g of benzoyl peroxide. Yield - 95%; Acid Index - 74; Viscosity - 2.08 cp (5% DMF at 34.6° C).

EXAMPLE 4

The method of Example 1 is repeated except that the monomers employed were 10 g of crotonic acid, 75 g of vinyl acetate, 12 g of allyl dimethyl propanoate and 3 g of allyl dodecanoate, in the presence of 1.2 g of benzoyl peroxide. Yield - 95%; Acid Index - 71; Viscosity - 1.77 cp (5% DMF at 34.6° C). MW = 19,000.

EXAMPLE 5

The method of Example 1 is repeated except that the monomers employed were 10 g of crotonic acid, 75 g of vinyl acetate, 10 g of allyl dimethyl propanoate and 5 g of allyl dodecanoate, in the presence of 1.2 g of benzoyl peroxide. Yield - 90%; Acid Index - 72; Viscosity - 1.99 cp (5% DMF at 34.6° C).

EXAMPLE 6

The method of Example 1 is repeated except that the monomers employed were 10 g of crotonic acid, 75 g of vinyl acetate, 12 g of allyl 2,2-dimethyl pentanoate and 3 g of vinyl dodecanoate, in the presence of 2 g of benzoyl peroxide. Yield - 95%; Acid Index - 71; Viscosity - 1.86 cp (5% DMF at 34.6° C).

EXAMPLE 7

The method of Example 1 is repeated except that the monomers employed were 7.5 g of crotonic acid, 77.5 g of vinyl acetate, 14 g of allyl dimethyl propanoate and 1 g of vinyl dodecanoate, in the presence of 1.2 g of benzoyl peroxide. Yield - 88%; Acid Index - 49; Viscosity - 2.25 cp (5% DMF at 34.6° C).

EXAMPLE 8

The method of Example 1 is repeated except that the monomers employed were 7.5 g of crotonic acid, 77.5 g of vinyl acetate, 12 g of allyl dimethyl propanoate and 3 g of vinyl dodecanoate, in the presence of 1.2 g of benzoyl peroxide. Yield - 90%; Acid Index - 55; Viscosity - 2.17 cp (5% DMF at 34.6° C).

EXAMPLE 9

The method of Example 1 is repeated except that the monomers employed were 77 g of vinyl acetate, 8 g of crotonic acid, 14 g of allyl dimethyl propanoate and 1 g of vinyl dodecanoate, in the presence of 1.2 g of benzoyl peroxide. Yield - 86%; Acid Index - 65; Viscosity - 2.25 cp (5% DMF at 34.6° C); MW = 21,000.

EXAMPLE 10

The method of Example 1 is repeated except that the monomers employed were 75 g of vinyl acetate, 10 g of crotonic acid, 14 g of allyl dimethyl propanoate and 1 g of vinyl dodecanoate, in the presence of 2 g of benzoyl peroxide. Yield - 83%; Acid Index - 67; Viscosity - 1.79 cp (5% DMF at 34.6° C); MW = 17,000.

EXAMPLE 11

The method of Example 1 is repeated except that the monomers employed were 66 g of vinyl acetate, 12 g of crotonic acid, 17 g of allyl dimethyl propanoate and 5 g of vinyl octanoate, in the presence of 2 g of benzoyl peroxide. Yield - 80%; Acid Index - 80; Viscosity - 1.71 cp (5% DMF at 34.6° C).

EXAMPLE 12

The method of Example 1 is repeated except that the monomers employed were 72 g of vinyl acetate, 12 g of crotonic acid, 15 g of allyl dimethyl propanoate and 1 g of vinyl octanoate, in the presence of 2 g of benzoyl peroxide. Yield - 79%; Acid Index - 78; Viscosity - 1.80 cp (5% DMF at 34.6° C).

EXAMPLE 13

The method of Example 1 is repeated except that the monomers employed were 79 g of vinyl propionate, 6 g of allyloxy acetic acid, 12 g of allyl 2,2-dimethyl pentanoate and 3 g of allyl dodecanoate, in the presence of 2 g of benzoyl peroxide. Yield - 85%; Acid Index - 29; Viscosity - 1.94 cp (5% DMF at 34.6° C).

EXAMPLE 14

The method of Example 1 is repeated except that the monomers employed were 80 g of vinyl acetate, 5 g of allyloxy acetic acid, 14 g of allyl 2,2-dimethyl octanoate and 1 g of allyloctanoate, in the presence of 2 g of benzoyl peroxide. Yield - 86%; Acid Index - 24; Viscosity - 1.95 cp (5% DMF at 34.6° C).

EXAMPLE 15

The method of Example 1 is repeated except that the monomers employed were 75 g of vinyl propionate, 10 g of crotonic acid, 10 g of methallyl dimethyl propanoate and 5 g of ethyl vinyl ether, in the presence of 2 g of benzoyl peroxide. Yield - 78%; Acid Index - 66; Viscosity - 2.04 cp (5% DMF at 34.6° C).

EXAMPLE 16

The method of Example 1 is repeated except that the monomers employed were 82 g of vinyl propionate, 7 g of allyloxy acetic acid, 10 g of methallyl 2,2-dimethyl octanoate and 1 g of dodecyl vinyl ether, in the presence of 2 g of benzoyl peroxide. Yield - 75%; Acid Index - 34; Viscosity - 2.1 cp (5% DMF at 34.6° C).

EXAMPLE 17

The method of Example 1 is repeated except that the monomers employed were 74 g of vinyl acetate, 10 g of crotonic acid, 15 g of methallyl 2,2-dimethyl pentanoate and 1 g of allyl acetate, in the presence of 2 g of benzoyl peroxide. Yield - 86%; Acid Index - 67; Viscosity - 1.86 cp (5% DMF at 34.6° C).

EXAMPLE 18

The method of Example 1 is repeated except that the monomers employed were 75 g of vinyl acetate, 10 g of crotonic acid, 10 g of methallyl dimethyl propanoate and 5 g of isopropyl vinyl ether, in the presence of 2 g of benzoyl peroxide. Yield - 83%; Acid Index - 68; Viscosity - 1.91 cp (5% DMF at 34.6° C).

EXAMPLE 19

The method of Example 1 is repeated except that the monomers employed were 80 g of vinyl acetate, 5 g of allyloxy acetic acid, 12 g of methallyl 2,2-dimethyl octanoate and 3 g of tertio butyl vinyl ether, in the presence of 2 g of benzoyl peroxide. Yield - 81%; Acid Index - 26; Viscosity - 1.97 cp (5% DMF at 34.6° C).

EXAMPLE 20

The method of Example 1 is repeated except that the monomers employed were 75 g of vinyl propionate, 10 g of crotonic acid, 5 g of allyl 2-isopropyl-2,3-dimethyl butyrate, 5 g of allyl dimethyl propanoate and 5 g of methallyl octanoate, in the presnece of 2 g of benzoyl peroxide. Yield - 79%; Acid Index - 67; Viscosity - 1.81 cp (5% DMF at 34.6° C).

EXAMPLE 21

The method of Example 1 is repeated except that the monomers employed were 75 g of vinyl acetate, 10 g of crotonic acid, 10 g of methallyl 2-isopropyl-2,3-dimethyl butyrate and 5 g of methallyl acetate. Yield - 84%; Acid Index - 69; Viscosity - 1.88 cp (5% DMF at 34.6° C).

EXAMPLE 22

The method of Example 1 is repeated except that the monomers used were 75 g of vinyl acetate, 10 g of crotonic acid, 5 g of allyl dimethyl propanoate, 5 g of methallyl dimethyl propanoate and 5 g of methallyl dodecanoate, in the presence of 2 g of benzoyl peroxide. Yield - 77%; Acid Index - 66; Viscosity - 1.75 cp (5% DMF at 34.6° C).

EXAMPLE 23

The method of Example 1 is repeated except that the monomers used were 75 g of vinyl acetate, 10 g of crotonic acid, 14 g of allyl dimethyl propanoate, and 1 g of vinyl dodecanoate, in the presence of 0.2 g of diallylether diethylene glycol and 1.2 g of benzoyl peroxide. Yield - 90%; Acid Index - 75.

EXAMPLES OF USE

EXAMPLE 24

A hair lacquer composition in accordance with the present invention is prepared by admixing the following components:

| Copolymer prepared in accordance with Example 1 | 8 g |
|---|---|
| 2-amino-2-methyl-1,3-propanediol, q.s.p. | pH 7 |
| Perfume | 0.1 g |
| Ethyl alcohol, q.s.p. | 100 g |

15 g of the above resulting solution are packaged, under pressure, in an aerosol container together with 50 g of trichlorofluoromethane and 35 g of dichlorodifluoromethane.

Similar effective hair lacquer compositions are prepared by replacing the copolymer of Example 1 in the above formulation with an essentially equivalent amount of the copolymers prepared in accordance with Examples 9-13.

EXAMPLE 25

A hair setting lotion composition in accordance with the present invention is prepared by admixing the following components:

| Copolymer prepared in accordance with Example 2 | 2 g |
|---|---|
| 2-amino-2-methyl-1-propanol, q.s.p. | pH 7 |
| Ethyl alcohol | 45 g |
| Water, q.s.p. | 100 g |

Similar effective hair setting lotion compositions are prepared by replacing the copolymer of Example 2 in the above formulation with an essentially equivalent amount of the copolymers prepared in accordance with Examples 14-18.

EXAMPLE 26

A hair lacquer composition in accordance with the present invention is prepared by admixing the following components:

| Copolymer prepared in accordance with Example 3 | 10 g |
|---|---|
| Triethanolamine, q.s.p. | pH 7 |
| Perfume | 0.2 g |
| Ethyl alcohol, q.s.p. | 100 g |

20 g of the above resulting solution are packaged, under pressure, in an aerosol container together with 45 g of trichlorofluoromethane and 35 g of dichlorodifluoromethane.

EXAMPLE 27

A hair lacquer composition in accordance with the present invention is prepared by admixing the following components:

| Copolymer prepared in accordance with Example 5 | 3 g |
|---|---|
| Isopropanol amine, q.s.p. | pH 7 |
| Perfume | 0.1 g |
| Ethyl alcohol | 12 g |

The above resulting solution is packaged, under pressure, in an aerosol container together with 49.7 g of trichlorofluoromethane and 35.3 g of dichlorodifluoromethane.

EXAMPLE 28

A hair lacquer composition in accordance with the present invention is prepared by admixing the following components:

| Copolymer prepared in accordance with Example 7 | 2 g |
|---|---|
| 2-amino-2-methyl-1,3-propanediol, q.s.p. | pH 7 |
| Perfume | 0.1 g |
| Isopropyl alcohol | 8 g |

The above resulting solution is packaged, under pressure, in an aerosol container together with 59 g of trichlorofluoromethane and 31 g of dichlorodifluoromethane.

EXAMPLE 29

A hair lacquer composition in accordance with the present invention is prepared by admixing the following components:

| Copolymer prepared in accordance with Example 6 | 3 g |
|---|---|
| 2-amino-2-methyl-1,3-propanediol, q.s.p. | pH 7 |
| Perfume | 0.1 g |
| Ethyl alcohol | 12 g |

The above resulting solution is packaged, under pressure, in an aerosol container together with 54 g of trichlorofluoromethane and 31 g of dichlorodifluoromethane.

A similar effective hair lacquer composition is prepared by replacing the 12 g of ethyl alcohol in the above formulation with 12 g of isopropyl alcohol.

EXAMPLE 30

A hair lacquer composition in accordance with the present invention is prepared by admixing the following components:

| | |
|---|---|
| Copolymer prepared in accordance with Example 8 | 2 g |
| 2-amino-2-methyl-1,3-propanediol, q.s.p. | pH 7 |
| Perfume | 0.1 g |
| Ethyl alcohol | 8 g |

The above resulting solution is packaged, under pressure, in an aerosol container together with 52.7 g of trichlorofluoromethane and 37.3 g of dichlorodifluoromethane.

Similar effective hair lacquer compositions are prepared by replacing the 2 g of the copolymer of Example 8 in the above formulation by an essentially equivalent amount of the copolymers prepared in accordance with Examples 19–22.

EXAMPLE 31

A hair lacquer composition in accordance with the present invention is prepared by admixing the following components:

| | |
|---|---|
| Copolymer prepared in accordance with Example 23 | 2 g |
| 2-amino-2-methyl-1-propanol | 0.167 g |
| Methyl cellosolve | 0.5 g |
| Ethyl alcohol | 12 g |
| Perfume | 0.2 g |

The above resulting solution is packaged, under pressure, in an aerosol container together with 52.36 g of trichlorofluoromethane and 32.773 g of dichlorodifluoromethane.

EXAMPLE 32

A hair setting lotion composition in accordance with the present invention is prepared by admixing the following components:

| | |
|---|---|
| Copolymer prepared in accordance with Example 15 | 2.2 g |
| Diethanolamine, q.s.p. | pH 7 |
| Ethyl alcohol | 42 g |
| Water, q.s.p. | 100 g |

Similar effective hair setting lotions are prepared by replacing the diethanolamine in the above formulation with triethanolamine and isopropanolamine.

What is claimed is:
1. Copolymer of
(a) an unsaturated acid having the formula

$$R-CH=CH-(CH_2-O-CH_2)_n-COOH$$

wherein $n = 0$ or 1, and when $n = 0$, $R = CH_3$ and when $n = 1$, $R = H$,
(b) a vinyl ester having the formula

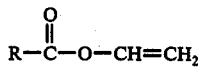

wherein R is $-CH_3$ or $C_2H_5$,
(c) at least one branched allyl or methallyl ester having the formula

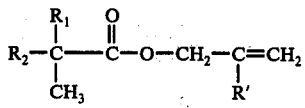

wherein R' represents hydrogen or $-CH_3$, $R_1$ represents a saturated hydrocarbon chain, linear or branched, having 1-6 carbon atoms and $R_2$ represents $-CH_3$ or $-CH(CH_3)_2$, with the proviso that the sum of the number of the carbon atoms in $R_1 + R_2$ is equal to or less than 7, and
(d) a monomer selected from the group consisting of
(i) a vinyl ether having the formula $$CH_2=CH-O-R_3$$

wherein $R_3$ is linear or branched alkyl having 1-12 carbon atoms,
(ii) a vinyl ester having a fatty chain and having the formula

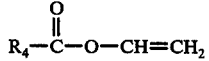

wherein $R_4$ is linear alkyl having 7-11 carbon atoms, and
(iii) a linear allyl or methallyl ester having the formula

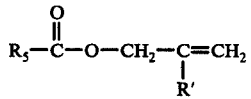

wherein R' is hydrogen or $-CH_3$ and $R_5$ is linear alkyl having 1-11 carbon atoms.

2. The copolymer of claim 1 wherein said unsaturated acid (a) is present in an amount of 2-15 weight percent, said vinyl ester (b) is present in an amount of 55-89.5 weight percent, said branched allyl or methallyl ester (c) is present in an amount of 8-20 weight percent and said monomer (d) is present in an amount of 0.5-10 weight percent.

3. The copolymer of claim 1 wherein said unsaturated acid (a) is present in an amount of 4-12 weight percent, said vinyl ester (b) is present in an amount of 65-85 weight percent, said branched allyl or methallyl ester (c) is present in an amount of 10-17 weight percent and said monomer (d) is present in an amount of 1-6 weight percent.

4. The copolymer of claim 1 wherein said unsaturated acid (a) is selected from the group consisting of crotonic acid and allyloxyacetic acid.

5. The copolymer of claim 1 wherein said vinyl ester (b) is selected from the group consisting of vinyl acetate and vinyl propionate.

6. The copolymer of claim 1 wherein said branched allyl or methallyl ester (c) is selected from the group consisting of allyl dimethyl propanoate, methallyl dimethyl propanoate, allyl 2,2-dimethyl propanoate, methallyl 2,2-dimethyl propanoate, allyl 2,2-dimethyl hexanoate, methallyl 2,2-dimethyl hexanoate, allyl 2,2-dimethyl octanoate, methallyl 2,2-dimethyl octanoate, allyl 2-isopropyl-2,3-dimethyl butyrate and methallyl 2-isopropyl-2,3-dimethyl butyrate.

7. The copolymer of claim 1 wherein said vinyl ether (i) is selected from the group consisting of methyl vinyl ether, ethyl vinyl ether, isopropyl vinyl ether, tertiobutyl vinyl ether, octyl vinyl ether and dodecyl vinyl ether.

8. The copolymer of claim 1 wherein said vinyl ester having a fatty chain (ii) is selected from the group consisting of vinyl octanoate, vinyl decanoate and vinyl dodecanoate.

9. The copolymer of claim 1 wherein said linear allyl or methallyl ester (iii) is selected from the group consisting of allyl acetate, methallyl acetate, allyl octanoate, methallyl octanoate, allyl decanoate, methallyl decanoate, allyl dodecanoate and methallyl dodecanoate.

10. The copolymer of claim 1 having a molecular weight ranging between about 15,000 to 40,000.

11. The copolymer of claim 1 neutralized with a base selected from the group consisting of monoethanolamine, diethanolamine, triethanolamine, isopropanolamine, morpholine, 2-amino-2-methyl-1-propanol and 2-amino-2-methyl-1,3-propanediol.

12. A process for preparing a copolymer comprising copolymerizing in an aqueous suspension in the presence of an effective amount of a polymerization catalyst, monomers consisting of (a) an unsaturated acid having the formula $$R-CH=CH-(CH_2-O-CH_2)_n-COOH$$

wherein $n = 0$ or 1, and when $n = 0$, $R = CH_3$ and when $n = 1$, $R = H$, (b) a vinyl ester having the formula

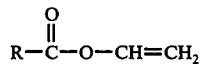

wherein R is $CH_3$ or $C_2H_5$, (c) at least one branched allyl or methallyl ester having the formula

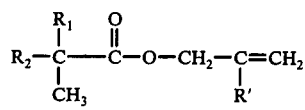

wherein R' represents hydrogen or $CH_3$, $R_1$ represents a saturated hydrocarbon chain, linear or branched, having 1-6 carbon atoms and $R_2$ represents $CH_3$ or $CH(CH_3)_2$, with the proviso that the sum of the number of the carbon atoms in $R_1+R_2$ is equal to or less than 7, and (d) a monomer selected from the group consisting of
(i) a vinyl ether having the formula $$CH_2=CH-O-R_3$$

wherein $R_3$ is linear or branched alkyl having 1-12 carbon atoms, (ii) a vinyl ester having a fatty chain and having the formula

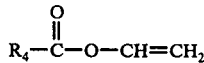

wherein $R_4$ is linear alkyl having 7-11 carbon atoms, and (iii) a linear allyl or methallyl ester having the formula

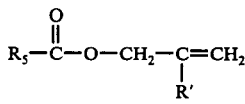

wherein R' is hydrogen or $CH_3$ and $R_5$ is linear alkyl having 1-11 carbon atoms.

13. The process of claim 12 wherein said polymerization catalyst is present in an amount ranging from about 0.5-6 percent by weight relative to the total weight of said monomers being polymerized.

* * * * *